United States Patent [19]

Gordon

[11] Patent Number: 5,255,585
[45] Date of Patent: Oct. 26, 1993

[54] VACUUM SYSTEM FOR CRYOSTATS
[75] Inventor: Abraham Gordon, Teaneck, N.J.
[73] Assignee: Instrumedics, Inc., Hackensack, N.J.
[21] Appl. No.: 762,619
[22] Filed: Sep. 19, 1991
[51] Int. Cl.[5] .............................................. B26D 7/18
[52] U.S. Cl. ......................................... 83/100; 83/168; 83/915.5; 62/320; 15/315; 15/415.1
[58] Field of Search ....................... 83/100, 168, 915.5; 62/320; 15/315, 415.1

[56] References Cited

U.S. PATENT DOCUMENTS

| | | | |
|---|---|---|---|
| 1,451,610 | 4/1923 | Gestas | 408/58 |
| 2,482,853 | 9/1949 | Ladd | 83/410.7 |
| 3,690,988 | 9/1972 | Ullberg | 83/915.5 X |
| 3,832,923 | 9/1974 | Lassmann et al. | 83/915.5 X |
| 3,880,047 | 4/1975 | Dosier | 409/134 |
| 3,885,320 | 5/1975 | Hodson et al. | 34/5 |
| 4,184,472 | 1/1980 | Benedicto et al. | 83/820 X |
| 4,361,957 | 12/1982 | Krötz et al. | 30/124 |
| 4,559,665 | 12/1985 | Fitzwater | 15/415.1 X |
| 4,650,505 | 3/1987 | Magdelain | 15/415.1 X |
| 4,695,339 | 9/1987 | Rada | 156/80 |
| 4,752,347 | 6/1988 | Rada | 156/382 |
| 4,956,892 | 9/1990 | Fawkes | 15/415.1 X |

FOREIGN PATENT DOCUMENTS 133778  2/1933  Fed. Rep. of Germany ........ 15/315

OTHER PUBLICATIONS

LKB 2250 PMV Cryo-Microtome, Microscopical Optical Consulting Inc., publication date unknown.
Reichert-Jung, Cryo Macrocut, publication date unknown.

Primary Examiner—Frank T. Yost
Assistant Examiner—Raymond D. Woods
Attorney, Agent, or Firm—Morgan & Finnegan

[57] ABSTRACT

A vacuum system for removal of debris in the form of shavings, particles, or the like has been developed for use inside of a cryostat to evacuate and collect such material as it is generated during specimen preparation using a microtome, also inside of the cryostat. The system includes a vacuum assembly unit containing a vacuum collection nozzle having a suction duct. The cold assembly unit is moveably positioned adjacent to the microtome knife so that debris is suctioned away and removed concurrent with or immediately after its production during cryotomy, and is captured in a cold primary filter. The frozen debris does not melt, but remains rigid while it freeze-dries and is trapped on the filter as cold air flows over and through it, thereby maintaining the collected waste material in a very porous state. This porosity permits the collection of a large volume of debris without clogging the cold filter, in contrast to the rapid clogging which occurs when such frozen debris melts, is suctioned into, collapses within, dries and seals off the pores of a warm filter. When required, the collection nozzle and attached assembly unit can be moveably positioned out of the way of the microtome knife. The system may also include a second bacteriological filter inside or outside of the cryostat to entrap any small quantities of fine debris which may pass through the primary filter after suctioning. When necessary, both types of filters can be efficiently, economically, and safely replaced and discarded.

27 Claims, 6 Drawing Sheets

DIRECTION OF AIR FLOW →

VACUUM SYSTEM FOR CRYOSTATS

FIELD OF THE INVENTION

The present invention relates to the field of removal of residual debris or shavings during thick or thin frozen section preparation, prior to microscopic examination, and using a cryostat containing a microtome.

BACKGROUND OF THE INVENTION

As used in histology, a cryostat is an apparatus consisting of a refrigerated or cooled chamber which contains a precision cutting device called a microtome. The cryostat is capable of maintaining a constant low temperature, especially below 0° C. (e.g. by means of mechanical refrigeration). The microtome is used to cut both thick and very thin slices or sections of specimens, especially frozen specimens, such as body tissue. Other types of samples such as teeth, bones, or sections of body organs are frequently sectioned. Tissue sections must be uniform in thickness and are cut as thin as $2\mu$ (microns or micrometers) or less (i.e. about 40 millionths of an inch or less). The prepared specimen sections are mounted on a microscope slide and can be stained, and then examined microscopically.

In a normal procedure for preparing a frozen histological specimen for microscopic examination, a tissue sample is brought into the laboratory for diagnosis. Embedding medium (e.g. aqueous saline solution, viscous aqueous solutions or gels) is routinely dispensed onto a specimen holder usually in the form of a small metal block. The specimen is either placed on top of or submerged into the embedding medium, and then is frozen, typically to about $-15°$ C. to about $-30°$ C., by any number of means. Once the specimen is frozen, the specimen holder is clamped tightly in the jaws of the microtome chuck (i.e. clamp). For sectioning frozen samples, the specimen holder is also maintained at a low temperature to avoid sample thawing. The low temperature is usually provided by the cryostat.

For cryogenic sectioning (also called cryotomy), a crank is either turned by the operator or is motor-driven and the microtome mechanism moves the specimen holder in an up and down motion. For each up-down cycle, the specimen holder or the microtome knife is advanced a pre-determined distance usually near the top of the up-cycle, typically between about 2 microns and about 20 microns. During the downward movement of the microtome specimen holder, the surface of the frozen tissue, as well as the surrounding embedding medium, are cut by the sharp microtome knife which is aligned at an appropriate angle. The surface produced by this cutting action is referred to as the cutting plane.

Typically, a sufficient quantity of frozen material must be trimmed away to form a flat surface exposing the section of interest. The trimming action is often accomplished by using a coarse setting of the microtome advance. When the appropriate level for collecting sections is reached, the microtome is reset for a smaller advance. The tissue section of interest is then cut and retrieved by the operator.

During the ordinary course of cryotomy, much waste and debris material is generated during the trimming phase of the procedure. This material is in the form of shavings, residual tissue debris, waste particles, and the like, frequently associated with the knife edge and/or generally dispersed throughout the cryostat during the cutting action. These shavings and pieces of specimen debris are frozen due to the low temperature of the cryostat, and are very thin and lightweight. The presence of this flimsy waste material is a source of several problems for operators of the microtome, for those who clean the cryostat, and when attempting to recover clean specimens, uncontaminated by pieces of the waste material.

First, depending on the source and type of the tissue specimen being sectioned, the production of the loose shavings and debris is potentially dangerous, especially when sectioning tissue specimens which may contain infectious agents. Loose or airborne shavings can easily come into contact with the operator. For example, if debris from a fresh tissue section contacts the skin, the section melts and leaves an invisible deposit. Thus, the operator may be unaware of this potential hazard. Such tissue debris or fragments can be transferred unknowingly from the hand to the mouth or other body parts of the operator, as well as to others with whom the operator has contact. If the shaving or section contacts the skin where the skin is cut or broken, infectious agents contained in the specimen may enter the tissues of the operator. A further potential hazard exists, since some airborne pieces of the shavings may be inhaled by the unsuspecting operator or by others in the vicinity.

Second, because the tissue debris is lightweight and plentiful, shavings and fragments generally become distributed throughout the interior of the cryostat after only a few minutes of operating the microtome. Moreover, the bulk of the debris and shavings accumulate in the immediate vicinity of the cutting edge of the knife blade. The presence of the waste material is also detrimental to the performance of the microtome, because loose particles can become trapped between sliding elements of the microtome and can create excess friction.

Third, the residual shavings can become lodged under inaccessible surfaces of both the cryostat and the microtome devices, making the process of cleaning-up very difficult. In order to clean the cryostat and microtome thoroughly, it is often necessary to remove the entire microtome from the cryostat chamber. This is a burdensome task and is frequently deferred until the build-up of the debris is pronounced and/or interferes with the operation of the microtome.

An ordinary vacuum cleaner device can be used to collect the loose shavings after sample sectioning. However, such vacuum cleaners pose several problems. Freshly cut shavings which have not dried out prior to the vacuum process will melt when they contact the inner walls of the hose or the warm filter medium situated inside of a typical vacuum cleaner. In such a case, after only a short period of operation, the melted debris will be aspirated into, collapse within, and seal off the pores of the filter as it dries, thereby making the vacuum cleaner inoperable. Even before the filter clogs, it is not uncommon for bacteria and mold to grow overnight on the inside wall of the hose and on the filter, producing an odor of rotting meat and an unsightly appearance to the hose. If a conventional vacuum cleaner is used at some time after the shavings and debris have already been generated, it is difficult to collect all of the shavings. Indeed, airborne shavings may have escaped much earlier during sample preparation and may have already dried onto the exposed skin of the operator, or may have been inhaled before the residual material is vacuumed away.

An ordinary vacuum cleaner, called a "HISTOVAC"™, has been equipped with a disposable wand, vacuum hose, and a filter trap in the hose, and is offered as a product to clean a cryostat. Such a vacuum cleaner unit and its hose-containing filter trap are located outside of the cryostat chamber. This type of vacuum cleaner suffers from all of the shortcomings described above. Specifically, since the vacuum cleaner and its filter are outside of the cryostat, the frozen flakes of waste material melt inside the warm or room-temperature vacuum hose and on the filter which is also warm or at room temperature. The filter is quickly clogged. Since vacuuming is done after the debris is generated, operator exposure can still occur and health risks due to accumulation and difficult clean-up, as mentioned above, are encountered. Furthermore, because of the melting of debris on the inner wall of the hose and on the filter during use, a considerable amount of hazardous material may adhere to and become lodged inside of the hose. As a consequence, the entire hose assembly must be discarded quite frequently. Repeated replacement of the entire hose assembly is inefficient and expensive.

The prior art does not adequately or cost-effectively solve the above-related problems associated with rapid clogging of the filter, or with the hazards of airborne waste material produced during the sectioning procedures. The prior art vacuum cleaner arrangement addresses after-the-fact clean-up of specimen waste material at room temperature and does not satisfy the need for trouble-free clean-up and removal of frozen debris during or immediately after its production.

SUMMARY OF THE INVENTION

The present invention is a vacuum system or apparatus that forms an integral part of a cryostat containing a precision microtome cutting device. Existing cryostats can be easily adapted to contain the present vacuum system, or the system can be constructed as an inherent part of newly-produced cryostats. The system is designed and employed for removing waste material and debris, concurrent with its production or immediately thereafter, during the preparation of thick or thin sections of tissue samples or other types of samples. Importantly, some critical components of the subject vacuum apparatus with its associated filters are housed inside of the cryostat chamber. The vacuum source can be located outside or inside of the cryostat chamber, and all parts of the system are connected in series with the vacuum source. The vacuum system described herein provides many advantages for the user, not the least of which are safety and economy.

The vacuum device in the system comprises a vacuum collection nozzle assembly unit which can be adjusted and positioned so that it is located in close proximity to the knife of the microtome in front of the microtome specimen holder. The vacuum collection nozzle, which is a part of the assembly unit, is placed in close proximity to the cutting plane of the microtome knife to ensure that virtually all of the specimen debris is captured by vacuum suction concurrent with or immediately following the generation of the debris during the trimming and cutting procedures. The vacuum nozzle may be secured to the microtome knife, if desired, through the use of a magnet, repositionable adhesive tape, or any other convenient attachment or mounting means. A foot-operated switch or other type of remote switch can be used to turn the vacuum motor on or off at will during trimming, cutting, and sample preparation. If an outside central vacuum source is used, the switch closure may operate a valve that would control the air flow.

In the subject vacuum system, multiple filters may be employed. Typically, a primary filter and a secondary filter are used, at least one of which is situated inside of the cryostat chamber. The secondary filter is typically an auxiliary bacteriological filter that is located downstream of the primary filter and is serially adjoined to the first filter. Any shavings or waste materials which are captured inside at least the primary filter remain stiff and frozen as long as the interior temperature of the cryostat remains about 0° C. or colder (i.e. at a temperature below the freezing point of water) during operation. The cold, dry air that is drawn over the waste debris and shavings retained inside the filter chamber causes the thin and lightweight material to freeze-dry in place within a few minutes. In addition, the entrapped debris and shavings remain stiff, freeze-dried, loosely-packed, and porous. The porosity of the freeze-dried material allows the cold air flow to continuously permeate the filter medium despite any small pressure drop, even after a large volume of debris has been trapped. In this manner, no substantial clogging occurs in the primary filter in this vacuum system.

For additional protection, especially when dealing with contaminated or harmful samples, the second, bacteriological filter, which can be directly or indirectly connected in series with the primary filter, captures and removes any microscopic debris which may have passed through the primary filter, and thus escaped entrapment in the primary filter media.

At least one collection hose connects the various components of the vacuum system and its associated filters. One or more collection hoses, or sections thereof, are routed internally within the cryostat chamber. Since the air temperature inside the cryostat is typically between about −15° C. and about −30° C., any shavings or waste material inside the internal hose remain rigid and frozen, and then are freeze-dried by the flowing cold air. One or more additional hoses in series may be located outside of the cryostat chamber and serve to connect the components of the system with the vacuum source.

In those cryostats which have prolonged defrost cycles, the temperature inside of the cryostat may occasionally rise above 0° C. Under these conditions, any shavings or debris which have not already been freeze-dried will melt on the inner walls of the hose or in the filter. Over a long period of time, the accumulation of this material in the hose or hoses situated upstream of the filters of this system may ultimately require the replacement of one or more of the hoses. For newer cryostats, the defrost cycle is more rapidly completed and the temperature inside the cryostat chamber rarely rises above 0° C. Therefore, using newer cryostats, the hose replacement schedule for the present system will be even less frequent.

A most important advantage of the subject vacuum system is that because the primary filter and the hoses connected with the filter are kept below the freezing point, rapid clogging of the filter by melting debris is prevented, thereby vastly extending the working lifetime of the filters.

Another important advantage of the vacuum system as described herein is that the vacuum nozzle is mounted directly proximal to the microtome cutting edge and is connected via the collection nozzle assembly unit, collection hose, filters, and vacuum hose to the vacuum source; thus, this system collects and traps waste material as soon as it is generated while sectioning a frozen specimen, provided that the vacuum switch is activated during the trimming operation. This vacuum system can also be used to remove debris shortly or some time after debris is generated, if desired. In addition, the system vastly reduces time-consuming clean-up after samples are sectioned.

Figure 1:
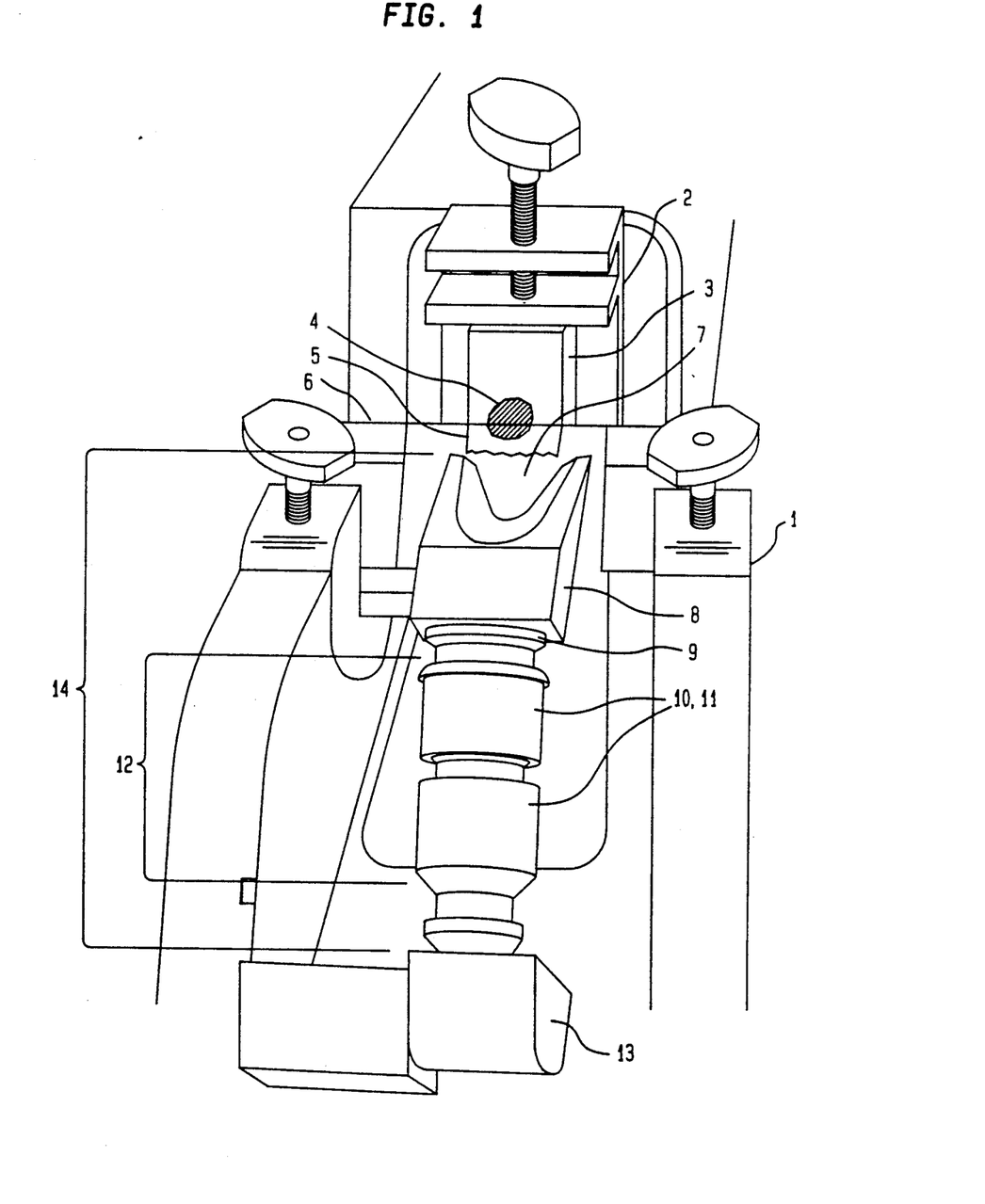
FIG. 1 is a detailed view of the arrangement of the vacuum collection nozzle assembly unit and its component parts, as positioned for use in relation to the microtome knife and in relation to the sample or tissue specimen which is held on the microtome block (i.e. the specimen holder).

Another significant advantage of the present vacuum system is that exposure of the user to potentially dangerous materials is greatly reduced. For example, with the subject vacuum system, bacteria- or virus-laden frozen shavings and debris which break off from an infected tissue sample are collected readily and efficiently just as soon as these waste materials are produced during the trimming and cutting phases of cryotomy. (FIG. 1). As a result of the immediate removal of potentially hazardous debris, and the doubly protective arrangement of the primary filter in combination with the secondary, bacteriological filter, a more contamination-free environment is provided. With the present invention, the overall safety of the operator and other is enhanced.

The present vacuum system for cryostats solves all of the aforementioned problems in a cost-effective, easy, and safe manner. The significant feature of the subject vacuum system is that it contains a nozzle assembly, collection hoses, and at least one filter, all of which operate at cryostat temperatures, thereby avoiding the problem of melting associated with room temperature vacuum devices. These and other advantages will become more readily apparent after a review of the drawings and the detailed description.

DETAILED DESCRIPTION OF THE INVENTION

The Vacuum Collection Nozzle Assembly Unit and Collection Hose

Figure 2:
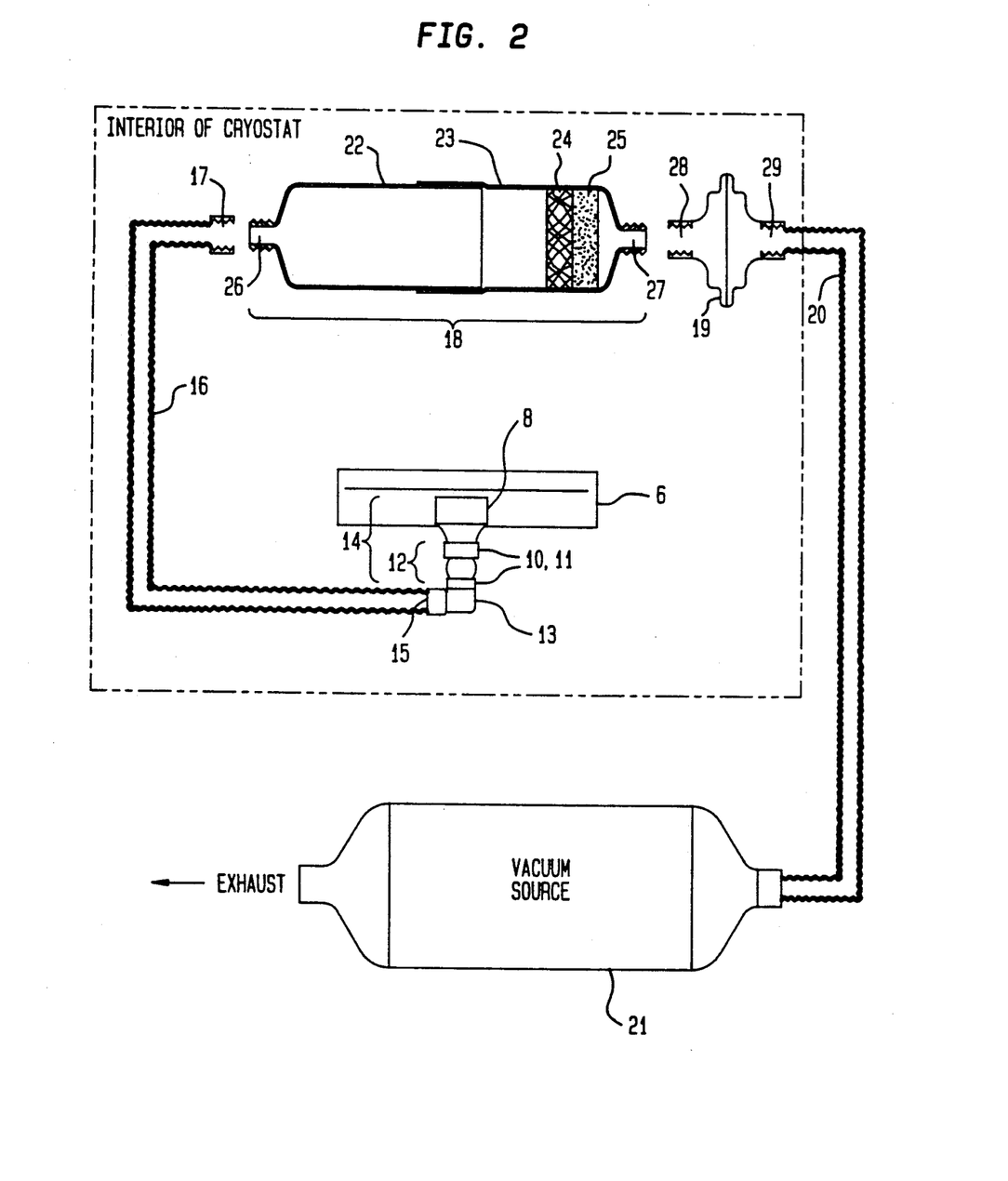
FIG. 2 is a schematic view of one arrangement of the collection nozzle assembly unit, the collection hose, the primary filter and, in this arrangement, the secondary filter internal to the cryostat chamber, the vacuum hose, and vacuum source, which in this depiction is external to the cryostat.

As reflected in FIG. 1 and FIG. 2, the present vacuum system or apparatus includes several serially connected components. The vacuum collection nozzle assembly unit (14) comprises several elements (8, 9, 10, 11, 12, and 13) which are securely interconnected. The assembly unit (14) attaches to the inlet end (15) of a collection hose (16) at the base of the assembly unit (14). The system is designed to be used in conjunction with a microtome (1) inside of a cryostat.

A vacuum collection nozzle (8) removes waste material or debris, such as shavings or flakes, or the like, concurrent with or immediately following the generation of this material. Most preferably, the collection nozzle (8) is positioned directly adjacent to the cutting plane of the microtome knife or cutting edge (6). Preferably, the collection nozzle (8) is positioned within about ½ inch of the cutting plane. The inlet of the collection nozzle (8) forms a suction duct (7) which is designed to be wide enough to capture both particulate debris and full specimen sections. Preferably, the duct is about ⅛ inch to about ¼ inch in height by about 1 inch to about 1½ inches in width.

FIG. 1 reflects a preferred fabrication of the collection nozzle assembly unit (14) and its interconnected elements. As such, the collection nozzle (8) is rotatably attached to a first swivel region (9) which is connected to a "telescoping section" (12). The telescoping section (12) is, in turn, rotatably connected to a second swivel region (13), lower down on the collection nozzle assembly unit (14). This lower swivel region (13) can be secured to the interior wall of the cryostat by means of two-sided adhesive tape or by any other suitable attachment means.

The telescoping section (12) is designed to accomodate the variable positions of the microtome knife (6) during the initial adjustments of the knife prior to sectioning a sample. For example, at the outset of cryotomy, the knife position on many microtomes must be changed relative to the surface of different sized blocks of frozen tissue. As a result, the overall distance between the collection nozzle (8) and lower swivel region (13) may also change in parallel with the changes in the knife position. It is the telescoping section (12) which provides the assembly unit (14) and its component elements with the means to accomodate for such positioning changes.

The collection nozzle (8), which has a relatively long, narrow duct (7) at its inlet, is designed to create a high velocity flow necessary to draw material into the nozzle (7) under vacuum. Downstream of the nozzle inlet, the duct undergoes a smooth transition into an opening having a circular cross-section. A swivel element (9), such as a hollow ball, rotatably fits into this spherical seat. The circular cross-section interior at the base of the nozzle (8) is designed to accept a commerically-available hose fitting (10). The hose fitting, which is preferably ¾ inches wide and made from vinyl-covered, flexible tubing, such as comprises a typical vacuum cleaner hose, fits snugly into the circular opening of the swivel element which forms the swivel region (9) and couples the collection nozzle (8) with the telescoping section (12). Two such hose fittings together with two lengths of rigid. "nesting" tubing constitute the complete and slidably moveable telescoping section (12) of the collection nozzle assembly unit (14). Preferably, the telescoping section is comprised of two cylindrical and concentric hose fittings or tubes (10), (11) which fit closely, but slidably, onto one or more lengths of rigid tubing which "nest" inside of the hose fittings, thereby allowing the in-and-out telescoping movement of the components of the telescoping section (12). The air space between the fittings and tubing is very small compared with the cross-sectional area of the collection nozzle, and thus does not short circuit the air flow and vacuum functions of the system. The length of engagement of the two cylindrical hose fittings or tubes will determine the maximum change in length of the collection nozzle and assembly unit; the range required to accomodate most microtome designs is about 1 inch to about 2 inches. Alternatively, the telescoping section can be fashioned from two molded, cylindrical pieces (e.g. (10) and (11)) slidably connected relative to one another by means of rigid "nesting tubing" so as to moveably accomodate the changes in length necessary during adjustments of the microtome cutting edge. In a variation, one of the molded cylindrical pieces of the telescoping section can be constructed to contain a cylindrical shaft or column of the appropriate length such that the other cylindrical piece fits snugly into this shaft and moveably slides in and out when positional changes of the collection nozzle and assembly unit are required and desired. In another variation, the telescoping section (12) and the accompanying hose fittings can be replaced by a single 90°-angle fitting which can be attached to the collection nozzle at its circular opening. Flexible, corrugated hose attached to the angled fitting can serve as both the swivel and the means for adjusting or positioning the collection nozzle assembly unit (14) as desired.

The swivel and telescoping regions (9, 10, 11, and 12) of the assembly unit (14) allow the unit as a whole, and the collection nozzle (8) in particular, to be moved toward and juxtaposed to the cutting plane. The moveable elements of the collection assembly unit (14) also allow the assembly unit (14) and collection nozzle (8) to be moved away from the microtome knife face, as may be necessary for easy access to the specimen section after cutting and for cleaning and/or replacing the knife edge (6). The lower swivel region (13) is connected to the intake end (15) of the collection hose or tubing (16).

The collection nozzle assembly unit (14) is typically small and compact so as to fit easily inside the cryostat chamber and to be easily moved toward and away from the microtome knife as desired. Preferably, the entire collection assembly unit (14) is about four (4) inches or less in length. The size of each of the elements of the assembly unit ranges from about ¾ inches to about 2½ inches in length.

The collection nozzle assembly unit (14) is preferably constructed of a non-corroding, durable material such as flexible vinyl, polyethylene, or polypropylene corrugated or smooth tubing or hosing which is commercially available. Such tubing is preferably translucent, but may also be opaque. The individual elements of the collection unit are preferably fashioned out of this tubing or hosing. The ends of the tubes or hoses are adapted to fit snugly into cylindrical tubes or contain resilient fittings as discussed hereinbelow. Alternatively, the individual elements of the collection assembly unit may be molded separately and suitably adapted to snugly interconnect with each other in series.

The suction duct (7) and upper portion of the collection nozzle (8) are preferably made of clear or translucent plastic, or the like, most preferably a durable material, to enable the user to view the shavings that are evacuated into the nozzle (8). The other elements of the assembly unit, (8), (9), (10), (11), and (12) may be constructed from opaque material. However, these elements are also preferably translucent to permit the user to observe and monitor the debris flowing through, thereby enabling the user to visually monitor any potential problems of clogging and blockage of the system.

The individual elements of the vacuum collection nozzle assembly unit (14) can be disconnected and removed for cleaning purposes or replacement, if necessary.

In the vacuum system, the collection nozzle assembly unit (14) is connected in series to the the primary filter housing (18) by means of a collection hose (16). The output end (17) of the collection hose (i.e. the end of the collection hose opposite the intake end (15) attached to the base of the assembly unit (14)) is, in turn, connected to the interior primary filter housing (18). The primary filter housing (18) is typically connected, either directly or indirectly, to one end or inlet (28) of a secondary filter housing containing filter medium (19), most preferably a bacteriological filter medium. The secondary filter (19), most preferably a bacteriological filter medium. The secondary filter (19) can be situated either inside or outside of the cryostat apparatus and downstream of the primary filter (18). To complete the system, another hose (called a vacuum hose (20) herein), which is connected to the other end or outlet (29) of the secondary filter (19), attaches to the vacuum source (21) which can be located outside of the cryostat chamber. Thus, by virtue of the vacuum from the vacuum source, frozen shavings and debris (5) suctioned into the inlet of the vacuum collection nozzle (8) through the suction duct (7) are transported through the cold collection assembly unit (14) and attached collection hose (16), and become entrapped or lodged in a rigid but porous state on or in the filter media (24, 25) contained in the primary filter housing (18). Any microscopic particles or exceedingly small debris that escape initial entrapment and pass through the primary filter (18) are captured by the secondary filter (19). The temperatures of the collection assembly unit (14), nozzle (8), and all interconnecting hose or hoses (16) are equivalent to that inside of the cryostat so that the extraneous debris and waste material are continuously kept frozen as they are transported through the cooled system.

In one embodiment, the vacuum source (21), is external to the cryostat and also exhausts outside of the cryostat chamber as shown in FIG. 2. In an alternative embodiment and further described hereinbelow, a different type of vacuum production configuration is used, such that one or more of the components involved in generating the vacuum may be situated inside of the cryostat chamber.

It is envisioned that the present vacuum system can be used with the internal primary filter, and either with or without the secondary filter, which can be positioned inside or outside of the cryostat chamber, depending on the types of sample specimens being sectioned.

The collection and vacuum hoses (16, 20) can be made of any suitable, durable, and non-corroding material such as polyethylene, polypropylene, rubber, nylon, polyvinyl chloride, or the like. Most preferably, the collection and vacuum hoses will be transparent or translucent, flexible in the cold, operating temperature of the cryostat interior, chemically resistant, and easily replaceable. Preferably, the collection hose (16) will have an interior diameter of approximately ¾ inch. In addition, the collection hose will preferably be neatly fittable into the cryostat interior and will be able to tolerate the necessary flexing at the cold temperatures of the cryostat without breaking.

During cryotomy, when a specimen (4) on the microtome block face (3) is trimmed to the desired level and the specimen section is to be retrieved, the entire nozzle assembly (14) and attached hose or hoses (16) of the present vacuum system can be smoothly moved or "swung away" from the microtome knife (6). In the conventional method of section retrieval, a specimen section is guided onto the microtome knife face using a brush or an anti-roll device. A warm slide is then touched to the section causing the section to melt and adhere onto the slide by surface tension. A commercially-available system such as the Cryostat Frozen Sectioning Aid, produced by Instrumedics, Inc. of Teaneck, N.J., utilizes an adhesive tape to capture the section during the cutting step and can be used in conjunction with the present invention. Because the system's vacuum collection nozzle assembly unit (14) and its attached hose(s) (16) can be physically moved away from the microtome knife (6), the retrieval of specimen sections on slides or adhesive tape need not be hampered by the presence of the vacuum nozzle assembly unit (14) during the process of manipulating and recovering specimen sections.

After a specimen section is retrieved, further trimming may be required to obtain another section from the same specimen (4), but at a different level of the specimen. For this process, the collection nozzle assembly unit (14) is easily moved back into place and positioned directly adjacent to the cutting plane. The nozzle is again in the correct position for use during any re-trimming step and collects all of the additional shavings as they are generated. After all sections from a given specimen are prepared and retrieved from the microtome block (3) as desired, the collection nozzle (8) may be moved away from the microtome knife (6) and the microtome block (3) can be unclamped and removed from the microtome chuck (2). A new block containing another specimen can be clamped in place and the above-described operations and maneuvers can be adroitly repeated.

As depicted in FIG. 1 and described above, the vacuum collection assembly unit (14) preferably has swivel regions (9) and (13), and a telescoping section (12). The swivel regions and telescoping section permit the operator to position the collection nozzle (8) on or near the microtome knife (6), and after the knife is re-positioned, to cut sections of a new specimen secured on a new specimen block. In addition, if desired, the collection nozzle assembly unit (14), including the hose fittings (10), (11) forming the telescoping section (12), can be manually detached from the lower swivel region (13). The main collection nozzle assembly unit (14) can then be replaced by another nozzle assembly unit attached to a longer, flexible hose, typically about 15 inches to about 20 inches long, which would normally be stored in the bottom of the cryostat so that it remains cold prior to its use. This auxilliary hose has a conventional type of vacuum cleaner nozzle, about 6 inches to 8 inches in length, attached to one end and a hose fitting, similar to (10), attached to the other end. The hose fitting can be inserted into the lower swivel region (13) which was vacated by the removal of the main nozzle assembly unit. With this longer auxiliary collection hose and nozzle assembly unit, the operator is able to retrieve debris which may occasionally fall to the bottom of the cryostat during the sectioning procedure.

The interconnecting components of the present vacuum system are in series and are preferably attached and sealed to one another. FIG. 2 and the further description of the invention hereinbelow reveal that the present vacuum system satisfies the sealable attachment of its discrete component parts. Preferably, the end (17) of the collection hose (16) which attaches to the inner primary filter housing (18) is fashioned into a sealable locking or fastening terminus (17) or otherwise contains or is adapted to contain an interlocking mating connector. An example of such an interlocking mating connector is a threaded screw cap or a portion thereof which engages a reciprocal mating outlet or fitting or connector on the receiving end of another component in the system. This connector can be an integral part of the hose or can be permanently affixed, bonded, or pressed onto the end of the hose, or into the inside opening of the end of the hose.

By way of example, to adapt the ends of the hoses as effective, sealable locking connectors, the tops of ordinary bottle screw caps were cut away leaving only a ring containing the threaded portion of the bottle cap. This ring was bonded into the end of the vacuum system collection hose. The screw caps were typically about ¾ inch in diameter and had standard bottle threads. These terminal caps served to tightly engage (i.e. screw onto) cylindrical bottles' threaded necks which comprised the inlet and the outlet ends of the primary filter housing (26, 27) as is further described hereinbelow.

The outlet end (27) of the primary filter housing (18) preferably comprises a mating locking outlet (27) which sealably fastens directly into a mating connector or locking means bonded or pressed onto or into the inlet end (28) of the secondary filter housing (19). The secondary filter housing (19) may also contain bonded or press-on fittings of a desired type, such as those previously described, at its inlet end (28) and at its outlet end (29). It is also contemplated that either the primary filter (18) or the secondary filter (19) or both may be sealably connected in series by means of a length of hose having locking mating connectors at its ends.

Since the present vacuum system is a complete system in series, the vacuum source (21) accesses all of the individual components of the system through their sealable interconnections as described above. In a preferred embodiment of the present system, the outlet end (29) of the secondary, or bacteriological, filter (19) preferably connects to the vacuum hose (20) leading outside of the cryostat through an opening in the cryostat wall. In this embodiment, the vacuum hose (20) connects to the vacuum source (21) which exhausts and is located external to the cryostat as depicted in FIG. 2.

The present vacuum system can be conveniently added to commercially-available cryostats by adapting or modifying the existing cryostat chamber, for example, to accomodate an external vacuum source serially connected to the other, internal components of the system. In addition, alternative designs of the vacuum system would allow the entire system to be easily placed and used in existing cryostats with either minimal or no additional modification of the cryostat. In such designs, any component of the vacuum system which is situated outside of the cryostat chamber may be serially connected to an interior component of the system through existing and accessible parts of the cryostat, for example, through the drain hole which is normally found in all cryostats. It is further envisioned that all variations of the vacuum system could be constructed and included as an inherent part of any re-modeled, newly-developed, newly-produced, or newly-built cryostat.

In one variation, the blower portion of the vacuum source can be situated inside of the cryostat chamber and the vacuum motor can be located outside of the cryostat. Such an arrangement would require that the vacuum source be built into existing cryostats through the chamber wall, for example. In another variation, a small vacuum pump can be used in conjunction with an accumulator tank inside of the cryostat. The pump operates continuously to build up vacuum inside of the tank. During operation as a vacuum, a valve connecting the tank to the vacuum system opens, and the tank draws in air from one or more hoses (i.e. those connected with the primary filter housing) located upstream in the system. In yet another variation which is especially suitable for use in already-existing cryostat models, a compressor pump can be located exterior to the cryostat and a high-pressure hose can be routed into the interior of the cryostat via the drain hole. The high-pressure hose can be connected to a special-purpose nozzle device which is located inside of the cryostat chamber and which generates a vacuum from a high-pressure air source, such as a Transvector Model 900 series, commercially available from Vortec Corporation, Cincinnati, Ohio. According to the manufacturer, the Transvector jet is a special-purpose nozzle in which a high pressure air stream is accelerated up to 1000 feet per second (f.p.s.) as the air stream passes through an annular orifice approximately 0.002 inches wide. This high velocity air stream entrains air from its surroundings and causes a large flow of air to occur. A Transvector may be able to entrain as much as 20 times the normal air flow in the primary jet. These devices, which are classified as high flow, low suction devices, are extremely quiet during operation. To avoid imposing a large heating load on the cryostat's cooling system, the air stream would have to be exhausted outside of the cryostat chamber.

It is also envisioned that the entire vacuum system, including the vacuum source, may be situated inside of the cryostat chamber, provided that the large heating load generated from the vacuum motor is adequately dissipated by the cooling system of the cryostat.

The Primary Filter Housing

Figure 3:
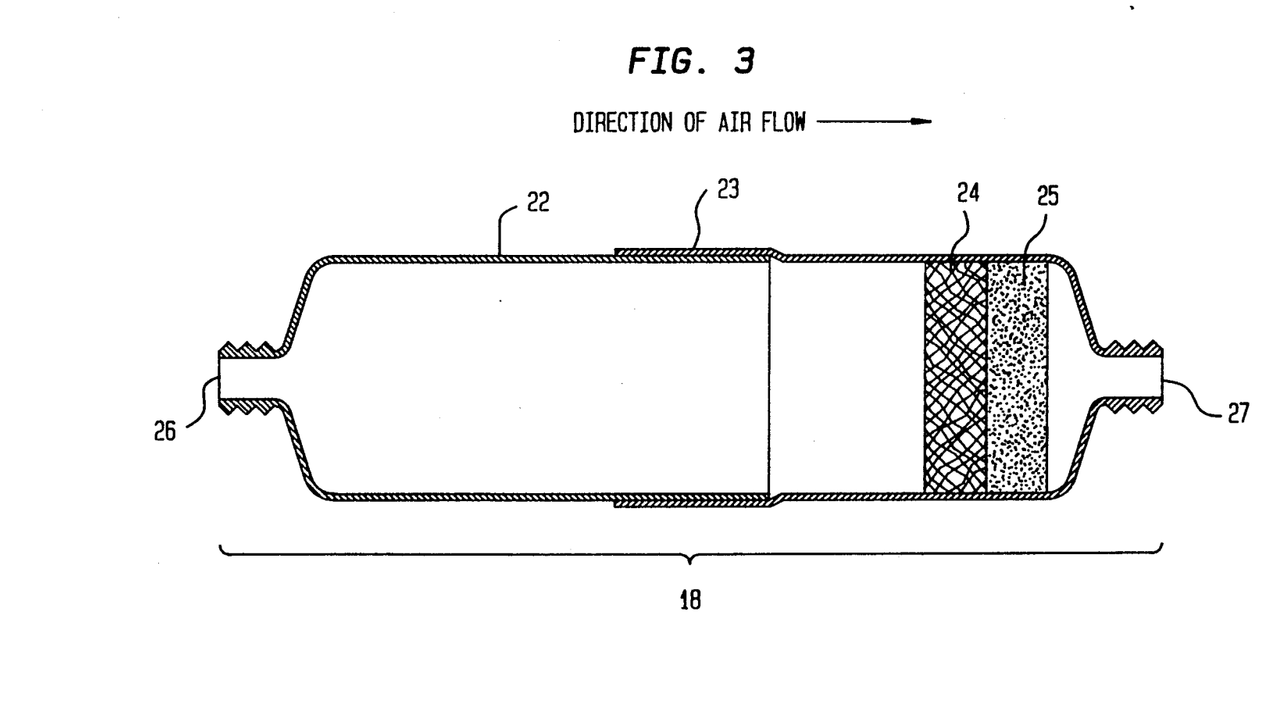
FIG. 3 is a cross-sectional view of the primary filter housing which contains filter media (e.g. coarse and fine filter media) at the end distal to the air intake end, and which is situated in the interior of the cryostat chamber. Air flow through the primary filter housing is such that virtually all debris transported therein remains rigid, frozen, and porous as it is retained on the internal filter media.
Figure 4:
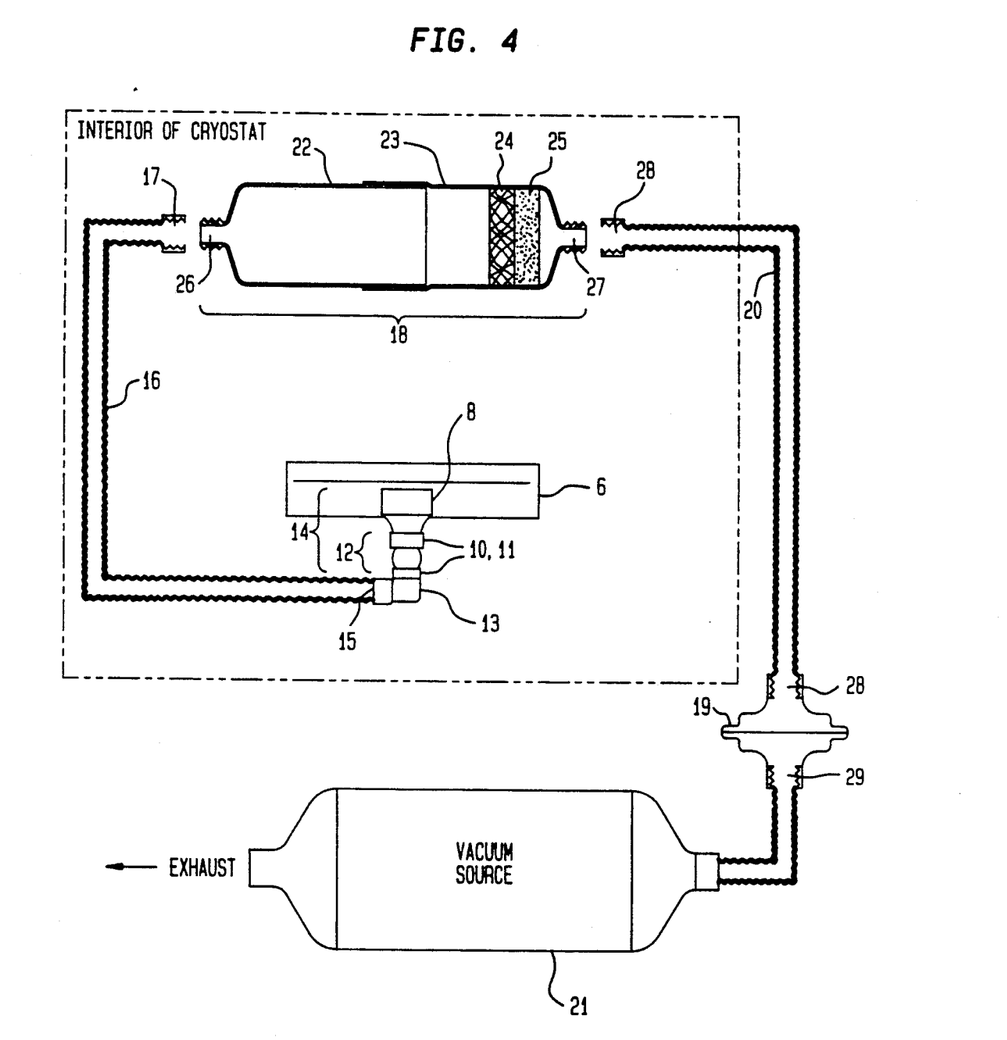
FIG. 4 is a schematic view of an arrangement of the collection nozzle assembly unit, the collection hose, the primary filter, and, in this arrangement, the secondary filter located external to the cryostat chamber and connected in series to the primary filter, the vacuum hose, and vacuum source which is exterior to the cryostat.
Figure 5:
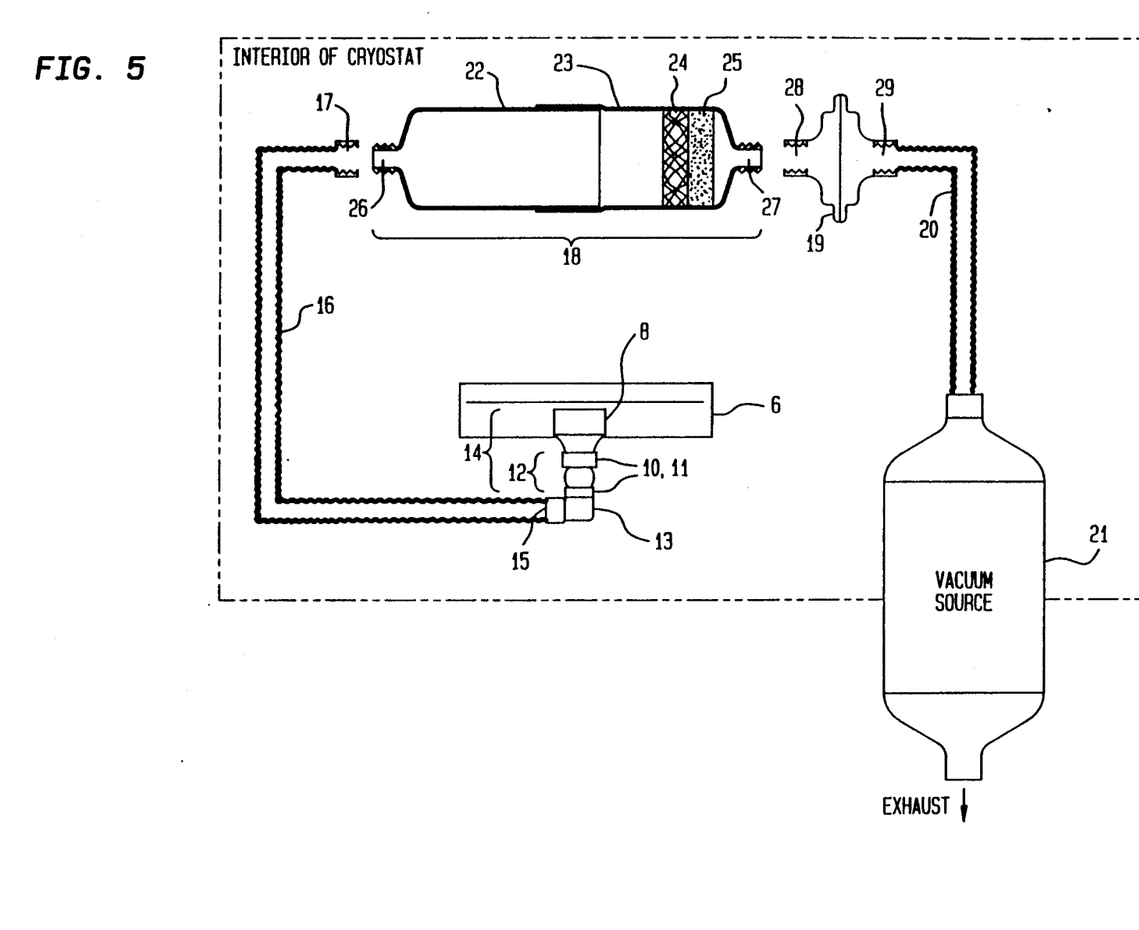
FIG. 5 is a schematic view of another arrangement of the vacuum system in which the vacuum source blower is located inside of the cryostat and is built into the cryostat through the cryostat wall. The vacuum exhausts to the exterior of the cryostat to maintain the frozen temperature of the cryostat interior.
Figure 6:
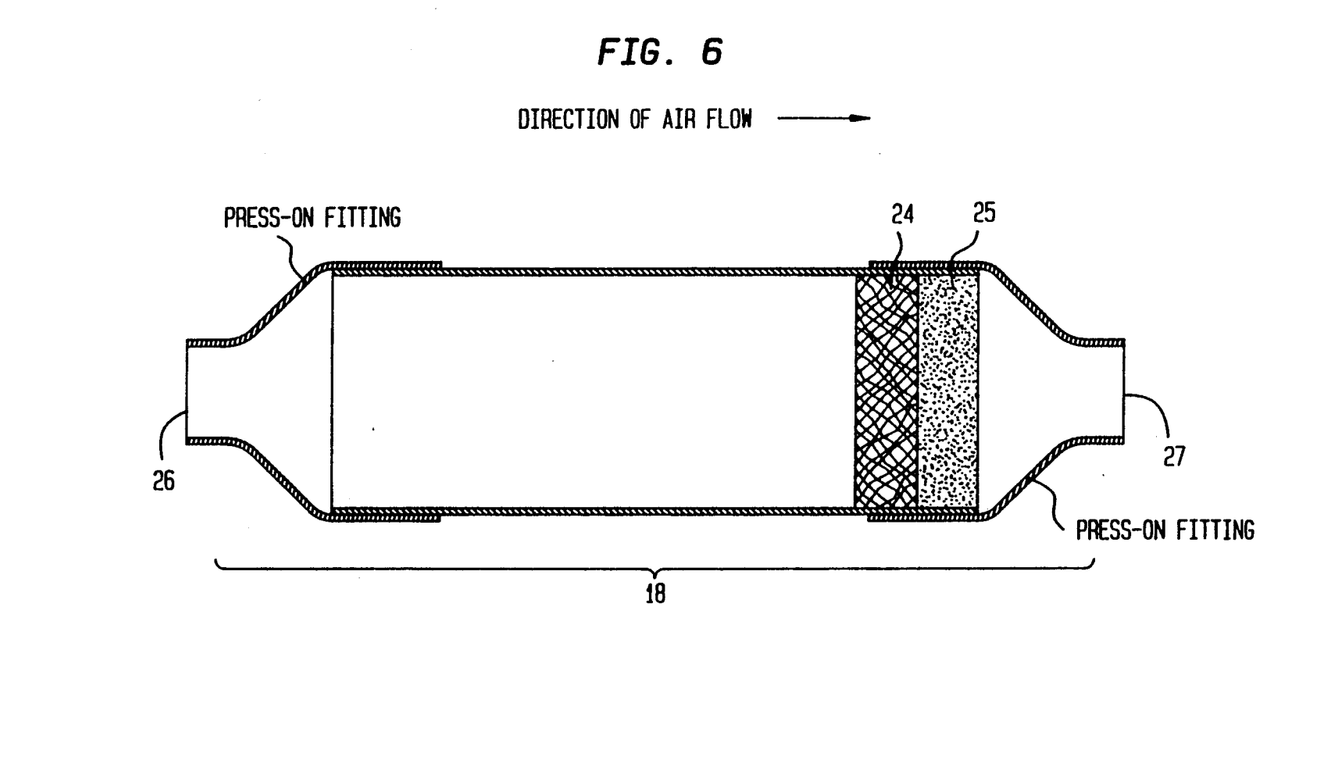
FIG. 6 is a cross-sectional view of the primary filter housing which comprises a cylindrical plastic tube, open at the inlet and outlet ends, onto which press-on fittings are sealably attached. The housing contains filter media (i.e. coarse and fine filter media) at the end distal to the air intake end, and which is situated in the interior of the situated in the interior of the cryostat chamber. Air flow through the primary filter is as shown so that virtually all debris transported therein remains rigid, frozen, and porous as it is retained on the internal filter media. The ends of the fittings have the ability to be sealed off when the internal filters are filled, and the entire used filter can be discarded.

As reflected in FIG. 2 and detailed in FIG. 3, the internal primary filter housing or casing (18) may be comprised of a cylindrical container or structure typically having two open and locking ports (i.e. locking means) at its opposite ends, thereby forming an inlet end (26) and an outlet end (27) of the primary filter housing unit (18). The housing can be machine-made, if desired, and molded into the designated cylindrical, open-ended components having locking outlets or ports at both ends, as described above. Since the primary filter housing (18) must contain filter media, it is preferable that the housing is initially made of more than one piece so that the filter media (24, 25) can be inserted, as is typical of such commercially-available filters. The separate, molded pieces can then be joined and bonded or otherwise fastened together to form the complete filter housing unit, containing the inner filter media. Indeed, other shapes and designs of the internal primary filter housing are contemplated as long as the housing fits easily within the confines of the cryostat chamber, contains the appropriate filter media, and can be easily and securely connected to the other parts of the vacuum system. In addition, the primary filter housing (18) may be connected to other components of the vacuum system via sealable press-on fittings at its termini, rather than via screw-type connectors. Additional "adaptor" fittings or locking connectors may be suitable attached to the original ends of the housing to change the connecting interface as desired.

Most simply, the primary filter housing can be made from two, hollow cylindrical containers such as bottles or the like (22, 23). The cylindrical containers are designed so that they fit snugly, one inside the other, with their locking outlets protruding at opposite ends (26, 27), as related in FIG. 2 and in FIG. 3. One cylinder (22) has a smaller diameter than the other so that a substantial portion of that cylinder nests firmly, yet rotatably, inside of the other cylinder with the body of the outer cylindrical container (23) as illustrated in FIG. 3., thereby insuring that the entire vacuum system is substantially air-tight.

By way of specific example, a primary filter housing was made from two commercially-available, clear, polyvinyl chloride, blow-molded bottles having a diameter of about 1½ inches and a length of about 3¾ inches (e.g. 4 fluid ounces). The bottoms of both bottles were cut away and the inside diameter of the end of one bottle was expanded so that it engaged the other bottle by at least 1 inch as shown in FIG. 3 (23). This arrangement permitted one of the bottles to rotate relative to the other and resulted in a filter housing having similar inlet and outlet openings formed by the protruding necks at opposite ends. The necks of the bottles so employed and arranged as shown in FIG. 3 were capable of receiving screw caps and were engaged by the ends of the collection hoses having portions of such open-top caps bonded thereto. In this manner, the filter housing was closed off and a leak-proof seal was formed.

Suitable non-corroding and durable materials from which the filter housing can be made are non-collapsable plastic, polypropylene, polyethylene, polyvinyl chloride, or other relatively rigid material. Such materials may be opaque, transparent, or translucent. Examples of such bottles are laboratory-grade bottles such as those commercially-available from laboratory or scientific supply and equipment vendors (e.g. Dynalon bottles from Aldrich Chemical Co., Milwaukee, Wis.; Nalgene Brand bottles from Sybron Corporation, Rochester, N.Y.; cylindrical laboratory containers from Fisher Scientific COmpany, Pittsburg, Penn., or from VWR, Pscataway, N.Y.).

The Filter Media of the Primary Filter Unit

The interal filter unit (18) contains filter media (24, 25) which function to trap frozen flakes and particles of debris or shavings that are drawn by vacuum into the collection nozzle and hose, and then pass into the filter housing. As depicted in FIG. 3, air flow through the filter allows frozen debris in the system to enter one inlet (26) of the primary filter housing (18), and become lodged on filter medium situated toward the outlet (27) of the housing. Vacuum air flow is minimally uninterrupted, since the freeze-dried debris remains porous and does not clog the filters, and therefore, does not block or severely retard air flow.

The filter media (24, 25) inside of the primary filter unit (18) preferably consist of a coarse, polyurethane open cell foam having an average pore size of about 1/10 inches (24), and a less coarse polyurethane open cell foam having an average pore size of about 1/32 inches (25). Other types and/or combinations of coarse and less coarse filter media or other suitable filter media with suitable pore sizes are also envisioned and can be used effectively inside of the primary filter housing. A disc of each type of filter foam medium is preferably "die cut" to have a diameter approximately ⅛ inch larger than the interior of the cylindrical filter housing. The two discs of filter media are typically arranged so that the more coarse filter medium is farthest away from the outlet end (27) of the filter housing (18) as illustrated in FIG. 2 and in FIG. 3. The pliancy of the filter material assures that the filter media are retained securely inside the primary filter housing (18).

The Secondary Filter

FIG. 2 reflects the presence of a second, auxiliary filter housing (19) with filter medium contained therein in the subject vacuum system. Preferably, this secondary filter is a bacteriological filter, connected in series with the primary filter (18) and located downstream from the primary filter housing (18). The secondary filter (19) can be situated either inside of the cryostat chamber or outside of the cryostat, as long as it is connected in series with the primary filter housing (18).

The purpose of the second bacteriological filter is further described hereinbelow. During the specimen cutting procedure, small quantities of extremely tiny pieces of the sample may break away as the pieces are drawn into the suction duct (7) of the vacuum collection nozzle inlet (8). In some instances, such microscopic fragments of a specimen may pass directly through the primary filter media and might ultimately become airborne as they exit from the vacuum exhaust. To alleviate this problem, insertion of the bacteriological filter, in series, ensures the capture of any residual material that might otherwise pass into the atmosphere. The bacteriological filter is especially valuable to supplement the activity of the primary filter and is preferably used in those cases in which samples may contain infections agents. In addition, the appropriate bacteriological filters obtained commercially have flow rates that are high enough so that the vacuum flow rate in the system is not significantly diminished.

As shown in FIG. 2, the secondary filter housing (19) is preferably constructed to contain sealable locking means at its opposite ends (28, 29), (i.e. its inlet and outlet ends), as described above for the outlets of the primary filter housing. Alternatively, the secondary filter housing (19) can contain press-on fittings which serve as interlocking mating connectors at its termini. The outlet of the secondary filter (29) can be attached to the vacuum hose by similar means.

Typically, bacteriological filters are constructed of two, rigid plastic halves which are welded together, capturing a layer of filter medium between the two halves. The sealable end fittings of the secondary filter are typically integral parts of each half. Additional "adaptor" fittings or locking connectors may be suitably attached to the original ends to change the connecting interface as desired. The entire secondary filter housing (19) with its internal bacteriological filter medium can be purchased as an assembled unit and can be easily replaced as a complete and assembled unit, when necessary.

The bacteriological filter provides an added safety feature for the present vacuum system and can be purchased from a commercial vendor. Preferably, the bacteriological filter used is the Hudson Bacteria Filter #1649 produced by the Hudson Oxygen Therapy Sales Corporation, Temecula, Calif. This preferred filter has 22 millimeter (mm) diameter fittings (approximately ⅞ inch diameter). The filter medium in the preferred bacteriological filter unit is electrostatically-charged "FILTRETE" TM produced by the 3M Corporation. According to the manufacture's specifications, this filter has a 99.9% bacteria filtration efficiency when tested with Staphylococcus aureus and a pore size of 0.3μ (microns). Other bacteriological types of filters are also suitable for use in the present system, as long as they are of an appropriate size, contain filter medium capable of retaining microscopic pieces of material, and support high flow rates. Bacteriological filters appropriate for the present system are available from Hudson Corporation, Temecula, Calif. as detailed above, and from the Pall Corporation, Glen Cove, N.Y.

Replacement of the Filters

Both the primary filter and the secondary filter units (FIG. 2, (18), (19), respectively) can be replaced together or separately. Replacing a used filter unit can be accomplished safely and easily. The life expectancy of the filters will depend on the volume of debris and shavings generated by the user; however, in the subject system, the primary filter rarely should have to be replaced more frequently than every week; the secondary filter will require less frequent replacement than the primary filter.

Preferably, the replacement primary filter housing (18) is equipped with locking ports (i.e. an inlet and an outlet) and suitable interlocking mating connectors (e.g. sealable locking caps, screw caps, locking means, fastening elements or fittings, or the like) in place at both ends (26, 27). Immediately prior to installation of the new replacement filter, the old, used filter cylinders can be rotated relative to each other (i.e. as described above, the exemplary cylindrical bottles rotated one inside the other) to disengage the locking means. If bottles having threaded necks are used to construct the filter housing, and bottle screw cap threads are bonded to the end of the collection hose or other attachment means, the screw cap portions are disengaged from the bottles' necks by a simple twisting action. Next, the locking connectors (e.g. the bottle screw caps) from the new, replacement filter are removed, and these connectors are tightened onto both locking outlets of the used or old filter housing which is then discarded in an appropriate biological waste disposal unit. The locking outlets of the new replacement filter housing are then ready to be sealably fitted into the receiving ends of the collection hose and the secondary filter (if attached thereto).

The sealable caps may be secured onto the old filter housing while it is still inside the cryostat, thus reducing an individual's risk of contacting any debris or waste material, or releasing waste material outside of the filter housing. With virtually no exposure of its contents, the contaminated primary filter can be properly disposed of in a re-sealable plastic bag along with other biological wastes.

In a similar manner, the secondary filter can be replaced with a new secondary filter whether inside or outside of the cryostat, and can be properly discarded.

The Vacuum Source

A. Vacuum Source Exterior to the Cryostat

For the present vacuum system having an exterior vacuum source, any vacuum cleaner source with adequate flow rate and very modest negative pressure may be used. Suitable for use are small portable vacuum cleaners having control switches either directly on the vacuum cleaner housing or as remote controls at some distance from the actual vacuum source. Other more complex or expensive vacuum sources can also be used.

By way of example, a vacuum source employed in the subject vacuum system used an approximately 1/12 horsepower motor which drove an exhaust blower and which was situated in a housing that was about 4 inches in diameter and about 8 inches in length. Such a vacuum source was inexpensive and was easily operated by means of an on-off switch.

B. Vacuum Source Interior to the Cryostat

One or more of the aforementioned alternative vacuum sources, or a combination thereof either partially or completely inside of the cryostat chamber, may also be suitable for generating a vacuum in the present system.

The Influence of the Use of Vacuum on Cryostat Temperature Control

While the motor of the exterior vacuum cleaner source is operating in the present vacuum system, cold air from inside the cryostat is drawn into the collection nozzle and is subsequently pumped to the outside of the cryostat. Room temperature air flows into the cryostat interior to replace this loss of air, thereby adding to the cooling load of the cooling system of the cryostat.

By way of example, when the present vacuum system, with the 1/12 horsepower external motor, was used continuously in a Minotome cryostat (available from Industrial Equipment Corporation, Needham, Mass.) or in a "TISSUE TEK II" ™ cryostat (available from Miles Corporation, Elkhart, Ind.) for more than 10 minutes, the cryostat interior temperature, which was registered on the display panel of the particular cryostat, typically showed that less than a 1° C. rise in temperature had occurred during such continuous use.

Under normal and routine conditions for cryogenic sectioning, the vacuum motor would be turned on for considerably less than 10 minutes at any one time. Therefore, it can be concluded that the added cooling load from the subject vacuum system having an exterior vacuum cleaner source is well within the cooling capacity of commercial cryostats. Cryostats with internal vacuum sources will often require higher capacity cooling systems to dissipate the heat generated by the motor of the vacuum source.

The examples described hereinabove are for illustrative purposes to further demonstrate the invention and are not meant in any way to limit the invention as set forth.

Although the foregoing invention has been described in some detail by way of illustration and example for purposes of clarity of understanding, it will be obvious to those skilled in the art that certain changes and modifications may be practiced without departing from the spirit and scope thereof, as described in the specification and defined in the appended claims.

What is claimed is:

1. A vacuum system for removing debris generated during sample preparation with a cryostat and a microtome within the cryostat, which comprises:
   (a) a means for suctioning the debris during sample preparation, said suctioning means situated interior to the cryostat; wherein said suctioning means draws an air stream under vacuum into said system;
   (b) a primary filter within a filter housing interior to the cryostat for entrapping and collecting the suctioned debris, said primary filter connected in series to said suctioning means and situated interior to the cryostat; and
   (c) a vacuum source;
   wherein said suctioning means and said primary filter are connected in series to said vacuum source; and wherein the air stream drawn into said suctioning means is exhausted outside of the cryostat.

2. The system as recited in claim 1, wherein a secondary filter for entrapping debris not retained on said primary filter is connected in series to said primary filter downstream of said primary filter, said secondary filter connected in series to said vacuum source.

3. The system as in claim 2, wherein said secondary filter is a bacteriological filter.

4. The system as in claim 3, wherein said secondary filter is situated interior to the cryostat.

5. The system as in claim 3, wherein said secondary filter is situated exterior to the cryostat.

6. The system as recited in claim 1, wherein said suctioning means collects the debris concurrent with generating the debris during cryotomy.

7. The system as recited in claim 1, wherein said suctioning means collects the debris immediately after generating the debris during cryotomy.

8. A debris removal vacuum system with an enclosed vacuum removal device and a vacuum source, especially to evacuate sample shavings generated from sample section preparation using a microtome cutting blade; the device and the microtome cutting blade interior to a cryostat, and the vacuum source exterior to the cryostat, the device comprising:
   a collection nozzle for suctioning debris;
   a collection nozzle assembly unit, said unit having a means for moveably positioning said nozzle near the cutting blade to place said nozzle into vacuum flow communication therewith;
   a collection hose connected to said assembly unit; and a primary filter housing connected to said collection hose for trapping debris;

wherein said device is serially connected to the external vacuum source.

9. The system as recited in claim 8, further comprising a secondary bacteriological filter for retaining microscopic debris that passes through said primary filter; wherein said bacteriological filter is connected in series to said primary filter and to the exterior vacuum source.

10. The system as in claim 9, wherein said bacteriological filter is situated inside of the cryostat.

11. The system as in claims 4 or 10, wherein said bacteriological filter is connected to said primary filter housing by means of a sealable locking connector.

12. The system as in claim 9, wherein said bacteriological filter is situated exterior to the cryostat.

13. A debris removal vacuum system for a cryostat and microtome, the microtome having a cutting edge for sample sectioning, comprising:

a vacuum collection nozzle, said nozzle positioned adjacent to the cutting edge of the microtome;

a collection nozzle assembly unit, wherein said assembly unit movably positions said nozzle near a plane with the cutting edge of the microtome;

at least one collection hose having two attachable ends;

a primary filter housing internal to the cryostat, wherein said housing contains debris-capturing filter media;

a bacteriological filter positioned downstream of said primary filter housing;

a vacuum hose having two attachable ends; and a vacuum source;

wherein the system is connected in series such that one end of said collection hose is attached to said nozzle assembly unit and the other end of said collection hose is attached to said primary filter housing; wherein debris arising from sectioning is transported by vacuum suction into said collection nozzle, through said collection assembly unit and said one collection hose, and onto the filter media inside of said primary filter housing; wherein said downstream bacteriological filter traps any microscopic debris that passes through said primary filter media; and wherein one end of said vacuum hose is attached to said bacteriological filter, and the other end of said vacuum hose is attached to said vacuum source.

14. The system as in claims 8 or 13, wherein said vacuum collection nozzle assembly unit consists essentially of:
(a) a suction duct on said collection nozzle;
(b) a first and second swivel region; and
(c) a telescopic section;

wherein said first swivel region connects said nozzle to said telescopic section, and wherein said second swivel region connects said telescopic section to said collection hose.

15. The system as in claim 14, wherein said collection nozzle is constructed of translucent, durable plastic.

16. The system as in claims 1, 9 or 13, wherein said primary filter housing has a sealable locking inlet and outlet at its opposite ends.

17. The system as in claim 16, wherein said primary filter housing contains coarse and fine filter media.

18. The system as in claim 16, wherein said primary filter housing comprises two cylindrical components, the cylindrical components being fitted one inside the other, and the locking inlet and outlet capable of connecting to mating locking connectors.

19. The system as in claim 16, wherein said primary filter housing comprises a plastic cylindrical structure, said cylindrical structure having open inlet and outlet ends; wherein the inlet and outlet ends are sealably fitted with connecting means; wherein said filter housing comprises a course filter and a fine filter, and further wherein said connecting means fitted onto the inlet and outlet ends are capable of being sealably closed when said filters are saturated with debris.

20. The system as in claim 8 or 13, wherein said collection hose contains a locking connector integral to one end, and wherein the locking connector sealably engages the locking inlet at one end of said primary filter housing.

21. The system as in claims 1 or 13, wherein said vacuum source is situated exterior to the cryostat.

22. The system as in claim 1 or 13, wherein said vacuum source is situated interior to the cryostat and exhausts outside of the cryostat.

23. A vacuum apparatus for debris removal during cryotomy, said apparatus interior to a cryostat, which comprises:
(a) means for suctioning debris produced during cryotomy;
(b) primary filter means connected serially therewith for retaining debris thereon; said primary filter means interior to the cryostat; and
(c) secondary filter means connected serially therewith for retaining microscopic debris which passes through said primary filter means.

24. The apparatus of claim 23, wherein said primary filter means contains coarse and fine filter media.

25. The apparatus of claim 23, wherein said secondary filter means contains bacteriological filter medium.

26. The apparatus of claim 25, wherein said secondary filter means is situated interior to the cryostat.

27. The apparatus of claim 25, wherein said secondary filter means is situated exterior to the cryostat.

* * * * *

UNITED STATES PATENT AND TRADEMARK OFFICE
CERTIFICATE OF CORRECTION

PATENT NO. : 5,255,585
DATED : October 26, 1993
INVENTOR(S) : Abraham Gordon

It is certified that error appears in the above-indentified patent and that said Letters Patent is hereby corrected as shown below:

The title page, should be deleted to be replaced with the attached title page.

Signed and Sealed this

Eighteenth Day of October, 1994

Attest:

BRUCE LEHMAN

*Attesting Officer*     *Commissioner of Patents and Trademarks*

United States Patent [19]
Gordon

[11] Patent Number: 5,255,585
[45] Date of Patent: Oct. 26, 1993

[54] VACUUM SYSTEM FOR CRYOSTATS
[75] Inventor: Abraham Gordon, Teaneck, N.J.
[73] Assignee: Instrumedics, Inc., Hackensack, N.J.
[21] Appl. No.: 762,619
[22] Filed: Sep. 19, 1991
[51] Int. Cl.⁵ ............................................. B26D 7/18
[52] U.S. Cl. ...................................... 83/100; 83/168; 83/915.5; 62/320; 15/315; 15/415.1
[58] Field of Search ................. 83/100, 168, 915.5; 62/320; 15/315, 415.1

[56] References Cited

U.S. PATENT DOCUMENTS

| | | | |
|---|---|---|---|
| 1,451,610 | 4/1923 | Gestas | 408/58 |
| 2,482,853 | 9/1949 | Ladd | 83/410.7 |
| 3,690,988 | 9/1972 | Ullberg | 83/915.5 X |
| 3,832,923 | 9/1974 | Lassmann et al. | 83/915.5 X |
| 3,880,047 | 4/1975 | Dosier | 409/134 |
| 3,885,320 | 5/1975 | Hodson et al. | 34/5 |
| 4,184,472 | 1/1980 | Benedicto et al. | 83/820 X |
| 4,361,957 | 12/1982 | Krötz et al. | 30/124 |
| 4,559,665 | 12/1985 | Fitzwater | 15/415.1 X |
| 4,650,505 | 3/1987 | Magdelain | 15/415.1 X |
| 4,695,339 | 9/1987 | Rada | 156/80 |
| 4,752,347 | 6/1988 | Rada | 156/382 |
| 4,956,892 | 9/1990 | Fawkes | 15/415.1 X |

FOREIGN PATENT DOCUMENTS 133778  2/1933  Fed. Rep. of Germany ........ 15/315

OTHER PUBLICATIONS

LKB 2250 PMV Cryo-Microtome, Microscopical Optical Consulting Inc., publication date unknown.
Reichert-Jung, Cryo Macrocut, publication date unknown.

Primary Examiner—Frank T. Yost
Assistant Examiner—Raymond D. Woods
Attorney, Agent, or Firm—Morgan & Finnegan

[57] ABSTRACT

A vacuum system for removal of debris in the form of shavings, particles, or the like has been developed for use inside of a cryostat to evacuate and collect such material as it is generated during specimen preparation using a microtome, also inside of the cryostat. The system includes a vacuum assembly unit containing a vacuum collection nozzle having a suction duct. The cold assembly unit is moveably positioned adjacent to the microtome knife so that debris is suctioned away and removed concurrent with or immediately after its production during cryotomy, and is captured in a cold primary filter. The frozen debris does not melt, but remains rigid while it freeze-dries and is trapped on the filter as cold air flows over and through it, thereby maintaining the collected waste material in a very porous state. This porosity permits the collection of a large volume of debris without clogging the cold filter, in contrast to the rapid clogging which occurs when such frozen debris melts, is suctioned into, collapses within, dries and seals off the pores of a warm filter. When required, the collection nozzle and attached assembly unit can be moveably positioned out of the way of the microtome knife. The system may also include a second bacteriological filter inside or outside of the cryostat to entrap any small quantities of fine debris which may pass through the primary filter after suctioning. When necessary, both types of filters can be efficiently, economically, and safely replaced and discarded.

27 Claims, 6 Drawing Sheets